United States Patent [19]

Bell

[11] Patent Number: 5,893,888
[45] Date of Patent: Apr. 13, 1999

[54] METHOD AND CONSTRUCT FOR PRODUCING GRAFT TISSUE FROM EXTRACELLULAR MATRIX

[75] Inventor: Eugene Bell, Boston, Mass.

[73] Assignee: Tissue Engineering, Inc., Boston, Mass.

[21] Appl. No.: 08/302,087

[22] Filed: Sep. 6, 1994

Related U.S. Application Data

[63] Continuation of application No. 07/926,885, Aug. 7, 1992, abandoned.

[51] Int. Cl.$^6$ .................................................. A61F 2/02
[52] U.S. Cl. ............................................................ 623/11
[58] Field of Search ........................... 623/1, 2, 11, 12, 623/15, 66; 424/422, 423, 424

[56] References Cited

U.S. PATENT DOCUMENTS

| | | | |
|---|---|---|---|
| 4,485,096 | 11/1984 | Bell | 623/16 X |
| 4,485,097 | 11/1984 | Bell | 623/15 X |
| 4,501,815 | 2/1985 | Reid et al. | 435/284 |
| 4,505,266 | 3/1985 | Yannas | 623/11 X |
| 4,642,292 | 2/1987 | Reid et al. | 435/240 |
| 4,645,669 | 2/1987 | Reid | 424/95 |
| 4,661,111 | 4/1987 | Rooslahti | 623/11 |
| 4,776,853 | 10/1988 | Klement et al. | 8/94.11 |
| 4,795,459 | 1/1989 | Jauregui | 623/11 X |
| 4,801,299 | 1/1989 | Brendel et al. | 623/1 |
| 4,837,285 | 6/1989 | Berg et al. | 530/356 |
| 4,902,508 | 2/1990 | Badylak et al. | 424/95 |
| 4,950,483 | 8/1990 | Ksander et al. | 424/422 |
| 4,969,912 | 11/1990 | Kelman et al. | 623/66 |
| 5,024,841 | 6/1991 | Chu et al. | 424/422 |
| 5,026,381 | 6/1991 | Li | 623/12 |
| 5,043,426 | 8/1991 | Goldstein | 424/423 X |
| 5,110,604 | 5/1992 | Chu et al. | 424/422 X |
| 5,171,273 | 12/1992 | Silver et al. | 623/13 |
| 5,192,312 | 3/1993 | Orton | 623/11 X |
| 5,201,745 | 4/1993 | Tayot et al. | 623/11 |
| 5,378,469 | 1/1995 | Kemp et al. | 424/423 |
| 5,562,946 | 10/1996 | Fofonoff et al. | 427/2.31 |

FOREIGN PATENT DOCUMENTS 0358506  3/1990  European Pat. Off. .

OTHER PUBLICATIONS

Stephen M. Edgington, *Bio/Technology*, 10:855–860, Aug. 1992 "3-D Biotech: Tissue Engineering".

Githens, S. III, et al., "Ducts of the Rat Pancreas in Agarose Matrix Culture," In Vitro, 16(9):797–808 (1980).

*Primary Examiner*—David Isabella
*Attorney, Agent, or Firm*—Scott D. Rothenberger; Lahive & Cockfield, LLP

[57] ABSTRACT

Using connective tissues as starting materials, a method is described for producing matrix particulates. The invention includes an embodiment wherein the matrix particulate are seeded with living human cells or with cells of other species. Further, the invention encompasses fusing the particulates to constitute composites of various shapes, or holding them together in a porous container made of membranous biopolymers. The particulates or composites can be used as tissues for grafting or as model systems for research and testing. The invention also encompasses the spinning of threads in which the matrix particulates are components.

10 Claims, No Drawings

METHOD AND CONSTRUCT FOR PRODUCING GRAFT TISSUE FROM EXTRACELLULAR MATRIX

RELATED APPLICATION

This application is a continuation of application Ser. No. 07/926,885 filed on Aug. 7, 1992, abandoned, which is incorporated herein by reference in its entirety.

BACKGROUND OF THE INVENTION

The use of synthetic materials such as polyester fiber (DACRON™) or polytetraflurorethylene (PTFE) (TEFLON™) as implants designed to replace diseased or damaged body parts has been extensive. These materials have however, enjoyed limited success. This has been due to the poor biocompatibility of these materials which among other problems, frequently initiate persistent inflammatory reactions. Additionally, the failure of the body to integrate these materials, because they do not break down and do not lend themselves to remodeling by tissue cells that may come into contact with them, causes further problems.

Efforts to use animal or human materials have also been unsatisfactory when these materials are cross-linked by formaldehyde or glutaraldehyde, for example. The process of generalized aldehydic cross-linking renders biomaterials sufficiently unrecognizable to tissue cells so that normal remodeling and integration are not promoted. Similarly, other types of chemical processing of animal or human biomaterials, such as extraction with detergents, or hypertonic buffers or hypotonic buffers can alter them to the degree that they are ineffective in promoting angiogenesis and in stimulating repair and remodeling processes needed for the conversion of an implant into a functional substitute for the tissue or organ being replaced.

A third approach has been that of reconstituting tissue and organ equivalents from structural matrix components, such as collagen, for example, that have been extracted and purified and combined with specialized cells. The process depends upon interactions between the cells and matrix proteins that the cells condense and organize. While tissue-like constructs have been fabricated and been shown to somewhat resemble their natural counterparts, they do not readily develop the matrix complexity characteristic of the actual tissues they are meant to imitate. See, for example, U.S. Pat. Nos. 4,485,096 and 4,485,097, E. Bell, 1984.

SUMMARY OF THE INVENTION

The present invention relates to a method of producing graft tissue by obtaining a desired connective tissue source and processing it to remove living cells without removing factors necessary for cell growth. The tissue is frozen or freeze dried and then fragmented, and the living cells removed to produce connective tissue matrix particulates. In the alternative, the tissue can be fragmented before freezing.

The invention also includes methods of producing graft tissue which comprise the above method with the additional steps, alone or in combination, of 1) again processing the connective tissue particulates to remove the cytoplasmic and nucleic acid components without removing the factors necessary for cell growth and differentiation; and 2) seeding the connective tissue particulates with cultivated cells under such conditions that the cells adhere to or populate the connective tissue particulates.

In one embodiment of the invention, the matrix particulates are seeded with selected cultured human or other cells. The resulting cell populated material can be fused into composites of various shapes, with or without the addition of growth and differentiation factors.

The present invention embodies a new method for preparing animal tissues as transplants designed to substitute for tissues or organs that are damaged or diseased. This is accomplished in such a way that their native complexity is preserved and thus allows them to be remodeled and integrated by the specialized cells with which they are brought into contact. In other words, because the matrix particulates of the present invention contain cell growth and differentiation stimulatory molecules, they provide the biomolecular signals needed for in vivo tissue repair. In contrast to methods previously described, the method of the present invention avoids the use of harsh reagents such as high salt, or delipidation reagents such as butanol/ether or detergents. The use of such reagents in methods previously described is responsible for removing from the connective tissue a great many factors whose presence we consider essential for stimulating repair and remodeling processes needed for the conversion of an implant into a functional substitute for the tissue or organ being replaced.

Advanced methods in in vitro cell cultivation permit expansion of small numbers of differentiated cells into large cell banks. Tissue matrix vehicles that can direct the organization and differentiation of these specialized cells for delivery to the human recipient in the clinic are needed. The present invention can be used to bring a disease such as diabetes under control by engineering and implanting reconstituted tissues or composites populated by cells with the appropriate functional capacity to overcome the problems caused by absent or insufficient insulin biosynthesis or its regulated delivery. For example, particulates of the present invention can be combined in vitro with cells from the islets of Langerhans, or with undissociated islets, to form a composite which is then implanted under the kidney capsule. Further, cell-populated matrix composites may be implanted directly, for example by using a hypodermic syringe or similar devise to deliver the composite to the desired site. This invention similarly may be used to treat Parkinson's disease by providing the patient with a tissue containing dopamine producing cells. One can also plate nerve cells on the particulates and allow a composite to form. This would be useful in the repair of neural tissue defects.

The method of this invention also has broad applications in the rebuilding of damaged or aberrant body structures such as skin, various tubular structures and skeletal structures such as bone, tendon and ligament. The invention may also be used to create connective tissue matrices to be used as tissue scaffolds which are populated by circulating cells after transplantation into the desired site. In one embodiment, the matrix particulates are mixed with a substance which can form porous membranous polymers containing the particulates, and then shaped. Matrix particulate-containing threads are one example of the many shapes which can be formed using particulates of the present invention. For example, the particulates can be mixed with collagen, or another bioabsorbable or nonbioabsorbable polymer, and extruded into a dehydration or coagulation bath containing absolute ethanol or acetone, or another dehydrating solution. The thread can also be subjected to dehydration by some other means, for example vacuum-drying. The particulates can also be coextruded with collagen or another polymer serving as a hollow fiber. Together, the particulates and the hollow fiber serve as a loaded hollow fiber with the particulates filling the core of the hollow polymer fiber. The threads produced in this manner can then be braided or woven to form fabrics or other complex constructs for implantation. In addition to the advantage provided by the high strength, flexibility and increased surface area of braided or woven threads, sleeves of the loaded hollow fiber threads can be made porous, thus allowing colonizing cells to occupy the surface of the thread and thereby contact the tissue matrix particles within the thread.

In a further embodiment, the method of the present invention is used to produce matrix particulates from fetal skeletal elements derived from animal sources, prior to mineralization. These fetal matrix particulates can be combined with osteogenic cells in cylindrically shaped collagenous containers to form skeletal constructs. The collagenous external surface of the containers can be plated with a second cell type associated with periosteal tissue. In a similar manner, a composite derived from dermal matrix particulates, or from a sheet of previously frozen matrix that has been perforated, can be over-plated with keratinocytes to form a skin-like construct.

DETAILED DESCRIPTION OF THE INVENTION

The invention includes a method of producing graft tissue which comprises obtaining a desired connective tissue source, then processing it to remove living cells without removing factors necessary for cell growth and differentiation. The cell-free connective tissue source is frozen or freeze-dried, and fragmented, either before or after freezing or freeze-drying, to produce connective tissue particulates. In the alternative, the tissue can be frozen or freeze-dried after fragmentation. The cell-free connective tissue particulates can be used as an implant for host cells to populate. The freeze-dried connective tissue can also be used without fragmentation, but perforated before use. According to this embodiment, the cell-free tissue can be used in the form of perforated sheets or strips without fragmentation.

The invention includes another method for producing graft tissue which comprises obtaining a desired connective tissue source and processing as above to remove living cells without removing factors necessary for cell growth and differentiation. The connective tissue source is frozen or freeze-dried, then fragmented to produce connective tissue particulates. The connective tissue particulates are seeded with cultivated cells under such conditions that the cells adhere to and populate the connective tissue particulates. In one embodiment of the present invention, the connective tissue particulates are seeded with cultivated cells and then packed into a preformed porous polymeric container. This method can also include the optional step of further processing the connective tissue particulates before they are seeded, in order to remove nucleic acids without removing other factors necessary for cell growth and differentiation. Further processing can include contacting the connective tissue particulates with nuclease preparations.

The invention includes another method for producing graft tissue which comprises obtaining a desired connective tissue source and processing as above to remove living cells without removing factors necessary for cell growth and differentiation. The connective tissue source is then frozen or freeze-dried and fragmented to produce connective tissue particulates. In the alternative, the cells can be removed prior to fragmentation. The particulates are mixed with a porous polymer, such as collagen or other bioabsorbable or nonbioabsorbable polymers, then extruded to form threads composed of the polymer and the connective tissue particulates. The threads of the invention can be either mixed fiber (in which the thread is comprised of a mixture of the polymer and the cell matrix particulate), or loaded hollow fiber (in which the thread is comprised of a core of cell matrix particulates surrounded by a porous polymer sleeve). These threads are then braided or woven to form fabrics or other complex constructs for implantation. The sleeve of the loaded hollow fiber threads is porous, thus allowing colonizing cells to occupy the surface of the thread and thereby contact the tissue matrix particles within the thread.

The invention encompasses another method of producing graft tissue which comprises obtaining a desired connective tissue source and processing to remove living cells without removing factors necessary for cell growth and differentiation. According to this method, the connective tissue source is frozen or freeze-dried, but not fragmented. Instead, the tissue is processed in the form of sheets or strips. These sheets or strips are frozen or freeze-dried, then thawed and perforated to allow cells to infiltrate the tissue. In one embodiment, the connective tissue sheets or strips are seeded with cultivated cells under such conditions that the cells adhere to and populate the sheets or strips. The seeded sheets or strips can be further shaped or molded to form useful graft tissue. In another embodiment of the subject invention, the sheets or strips can be implanted into a host without first seeding with cultivated cells. According to this embodiment, the sheets or strips would provide a site for host cells to populate.

Fragmentation of the desired tissue can be achieved by freezing or freeze-drying, and then mechanically blending the frozen or freeze-dried tissue or mechanically crushing it between rollers. The desired tissue can also be fragmented by blending the tissue without first freezing it. An optional nuclease treatment is carried out for the purpose of digesting the nucleic acids released when the cells and cell nuclei are ruptured, which resulted from the treatment of cell removal. The connective tissue particulates are then washed and collected by the serial steps of centrifugation, resuspension, recentrifugation and resuspension.

The invention further encompasses a method wherein the connective tissue particulates obtained by the above methods are layered onto a synthetic porous membrane to a thickness which allows diffusion of nutrients to all the connective tissue particulates. One embodiment of this method includes an additional step of fusing the connective tissue particulates to form a composite using a fusing agent. The type of fusing agents which can be selected are known to one skilled in the art. In a preferred embodiment, in vitro cultivated cells are plated onto the connective tissue composite in a volume which will just cover the composite and allow transportation of nutrients. The cells are plated under conditions that allow the cells to populate or adhere to the connective tissue particulates. One or more than one cell type can be plated onto the composite.

The invention further includes a construct which is produced by any of the above methods, including a multi-cell construct.

The connective tissue source can be derived from bovine, ovine, porcine or marine animal connective tissues, as well as other species of vertebrates or invertebrates. The invention further includes connective tissues which are derived from a variety of body parts or tissues. In a preferred embodiment of the invention connective tissue is derived from embryonic or fetal tissues. Embryonic and fetal tissues are advantageous because they include various biomolecular factors which are present in normal tissue at different stages of cell development. The factors present in fetal tissues include, for example, factors necessary for cell division, differentiation and tissue morphogenesis.

The connective tissue matrix particulates derived through the above methods can be seeded with selected cultured human or other cells. The resulting cell-populated matrix can be fused into composites of various shapes, with or without the addition of growth and differentiation factors.

In a preferred embodiment of the invention the matrix particulates are selected to match the tissue being fabricated. For example if a skin replacement is the objective, preferably dermal matrix would be particularized and a composite with dermal cells constructed. If neural tissue replacement is the goal, preferably embryonic or fetal central nervous system connective tissue matrix would be chosen for combination with the appropriate cells to form a composite.

The processing steps of the above methods are performed in order to remove cells from the selected animal tissues, thereby producing connective tissue matrix particulates. There are many methods known in the art for removing cells from connective tissue. The following are examples of some of these methods. These examples are not intended to be an exhaustive list, but are merely examples of some of the known methods. The choice of method and the sequence of treatments depend on the type of tissue being processed.

In one method for removing cells from the connective tissue, the tissue is scraped with a blade or blade-like instrument. The tissue can also be passed successively between parallel rollers, where the rollers are brought closer together in successive steps thereby squeezing out soft components including cells. The tissue can also be treated with enzymes, particularly nucleases. Additionally, the tissue is passed through a freeze-thaw, or freeze-dry-thaw cycle in order to disrupt the living cells. These methods can also be employed to remove remaining cytoplasmic and nuclear components in connective tissue particulates produced by fragmentation of the connective tissue source.

The freezing and/or freeze-drying, and fragmentation steps are done to produce particulates and to further free the tissue of undesirable components. Methods for sterilizing processed tissues are known to one skilled in the art and include contacting the tissue with a peracetic acid solution, preferably about a 0.5% solution, and washing the tissue in a sterile buffer, preferably sterile phosphate buffered saline. The tissue can then be freeze-dried by being brought to the temperature of liquid nitrogen, then fragmented under sterile conditions. Fragmentation at low temperature can be carried out in many ways known to those skilled in the art. Fragmentation methods could include a shearing device, such as a mechanical blender, or mechanically crushing the tissue between rollers to yield particulates of such a size so as to allow for vascularization upon implantation. In a preferred embodiment of the invention, the particulates are between about 50 and about 300 micrometers in diameter, but for some applications the particulates can be as small as 5–10 microns. Depending on the starting tissue type, further nuclease cleaning and washes followed by centrifugation and resuspension in fresh phosphate buffered saline can be carried out in an effort to minimize the presence of components which are immunogenic.

In another embodiment of the invention the tissue can be dehydrated chemically with acetone, absolute alcohol or hydrophilic polymers such as carbowax, and then fragmented.

In a preferred embodiment of the invention the particulates are further treated by seeding the matrix with cells. Preferably one would use human cells for populating the matrix, but the invention is not limited to human cells. In one embodiment the seeding process is carried out by rehydrating the matrix particulates using tissue culture medium, with or without growth and differentiation supplements added, and allowing the particulates to swell to equilibrium with their fluid environment.

In another embodiment of the invention the matrix particulates are populated with cells of one, or more than one phenotype in a bioreactor, spinner flask or other similar device. The number of cells used and the time of residence in the device depend on cell attachment time and the desired degree of coverage of the particulate by the cells. These parameters will vary depending on the type of cell used and the cell density required for the final product. The particular parameters for each cell type will be apparent to one skilled in the art. In a preferred embodiment of the invention the starting cell density is on the order of about $10^4$ to about $10^6$ cell per ml.

In a further embodiment of the invention the particulates are fused into composites of various shapes with or without the addition of growth and differentiation factors. This step can be carried out on particulates which have been seeded with cells, or on particulates which do not contain cells. In the latter case the fused matrix composite can be seeded with cells after the particulates are fused into composites. The matrix composite, with or without cells, is then layered onto a synthetic porous membrane. Examples of a synthetic porous membrane, for illustrative purpose only and not to limit the invention in any way, include membranes made of polycarbonate, for example in a transwell arrangement, or a bioabsorbable polymer, such as a porous collagen sheet that lines a mold having a porous membrane for a bottom to hold the collagen sheet and permit passage of medium from below. The membrane may also be made of other bioabsorbable polymers such as poly-l-lactate. In one embodiment of the invention the particulates are layered in a single layer. In a preferred embodiment the layer is less than about 0.5 millimeters in thickness.

If the matrix has been seeded with cells, the thickness of the layer must be controlled in such a way so as to ensure that the necessary nutrients may flow to the cells. The seeding of the matrix is carried out by applying cells in suspension directly onto the particulate composite in a volume that will just cover the composite but not run off it, under such conditions that the cells populate the matrix.

Non-limiting examples of a few of the ways in which the porosity of the composites can be controlled include: limiting cell growth, limiting crosslinking, and mechanically, by placing a brush-like device with spaced TEFLON™"hairs" onto the substrate prior to delivering the particulates to it. If the last expedient is used the sheet will form around the microposts or "hairs", thereby creating holes when the "hairs" are removed.

If the matrix is seeded with cells and then incubated for a period of time in tissue culture medium, the construct will be in the form of a coherent sheet that can be handled alone or, for example, by the porous collagen membrane on which it formed. In a preferred embodiment of the invention the incubation period is about 7–14 days. The collagen membrane can also be used to wrap the composite. The collagen membrane can be fixed to the composite, for example by suturing, so that a flat package is formed. The sheet can also be rolled around a shaft to form a tube at any stage in its development after it becomes coherent.

A further embodiment of the invention includes the use of multiple cell types combined with the composite by plating cells on either side of the composite, or by plating cells on the porous collagen membrane used to wrap the composite. Further, a layer of one cell type can be plated over a layer containing another cell type, or cells of different types may be plated together.

Still further the invention encompasses the case where the cell-laden particulates are packaged in a preformed porous collagen or other polymeric container of any desired shape. The container can be a rectangular box where, in a preferred embodiment, the box is not thicker than about 1.0 mm. Additionally the invention discloses the use of concentric tubes of differing radii where, in a preferred embodiment, the radii would differ by only by about 1.0 mm or less. It is also envisioned that other shapes can be used as well.

The containers can be reinforced by struts or other means to maintain uniform thickness. The frequency of the struts is preferably about 1–10 per mm square. The container can be made out of a collagen sheet with pores which are too small to allow particulates to escape. In a preferred embodiment, the pores measure about 30 to about 60 microns. After introduction of particulates through an end opening, the container can be sealed by suturing or other means.

In another embodiment of the present invention, the connective tissue particulates are formed into threads suitable for weaving or braiding. The threads can be woven into fabrics or other complex constructs for implantation. the braided or woven fabrics would provide a scaffold of matrix material for host cells to adhere to. In addition, the thread or fabrics produced from the threads, can be seeded with cells in vitro, as above, and then transplanted into the appropriate site in the host.

The threads of this invention can be either of the mixed fiber, or the loaded hollow type. Mixed fiber threads are made by mixing connective tissue particulates with a bioabsorbable or nonbioabsorbable polymer, then extruding the mixture, using, for example, a spinneret, to form a mixed thread. The hollow fiber thread comprises a core of connective tissue particles of this invention surrounded by a porous polymeric sleeve. The polymer used for producing the threads can be either bioabsorbable or nonbioabsorbable. In a preferred embodiment the polymer is collagen. After extrusion, threads of this invention are dehydrated and coagulated, for example by extrusion into a bath containing absolute alcohol, carbowax or acetone. The threads can then be annealed, for example by pulling the threads over rollers from the coagulation bath into an annealing bath containing a saline solution. The threads can then be dried and spooled, for example by pulling the threads over more rollers to dry, and then winding onto spools.

Exemplification

Animal sources are obtained for connective tissue matrix materials, such as organs, from porcine, bovine, ovine, marine or other animals. For example, to reconstitute an endocrine pancreas equivalent at least three organs can be used. The first is the pancreas itself, which would provide the tissue specificity of the matrix. The second is the duodenum or jejunum of the gut and the third is the skin.

The organs are packed on ice in sterile containers immediately after animal slaughter and transported to the laboratory. The pancreas is treated using the protocol for islet removal, that is, the pancreatic duct is cannulated and Hank's solution containing 2mg/ml collagenase (Type X, Sigma) and 2% fetal calf serum is injected. In addition the two arteries that supply the pancreas, the celiac and the superior mesenteric, are similarly perfused with a collagenase solution containing heparin to remove endothelium from the circulatory tree of the gland. Adequate cleaning of the pancreas may require heparinizing animals before slaughter. A compression device is used to gently knead the organ as it is perfused and reperfused in a sterile chamber in the cold.

In the course of recirculation the collagenase solution is gradually diluted. A fibrous network of ducts and vessels remains after collagenase digestion. After washing in phosphate buffered saline, the fibrous material is freeze-dried and mechanically fractured in an OMNIMIXER™ shearing tube. After thawing, the particulates are washed again and sterilized in 5.0% peracetic acid.

The objective of the freezing and fracturing procedure is to provide matrix particulates of between 100 and 200 µm in diameter. The islet of Langerhans of the pancreas, responsible for secreting insulin and other hormones, itself measures between 100 and 200 µm. The size of the particulates is also determined by the maximum allowable thickness of a tissue graft made to a host. The thickness must be consistent with survival after implantation in vivo. A diffusion distance greater than 0.5 mm is not desirable, because the graft must depend on diffusing tissue fluids for gas exchange and nutrients until it is vascularized. The goal is to produce particulates of relatively uniform size from the frozen tissue by a mechanical process that will not melt the material by frictional heating. Blending, grinding, crushing, and/or percussion in the cold at −30° C. or below are methods which can be used.

The particulates are then combined into aggregates with small clusters of cultivated cells, or are used as microbeads in a cell bioreactor in which cells from islet cell cultures are seeded. The cells attach to surfaces of the matrix microbeads in the bioreactor. The last mentioned strategy is useful as a means of expanding islet cell cultures; it can also serve as a means for constituting pseudo-islets.

The second example of an organ processed for its matrix is the jejunum or duodenum which is mechanically scraped after opening. As described by Badylak, et al., U.S. patent Ser. No. 4,902,508 (1990), the stratum compactum, about 100 µm thick, lying between luminal layers on one side and the muscular layers on the other, is delaminated from them, leaving an acellular collagenous connective tissue. The washed stratum compactum is particularized after freeze-drying as described above.

Similarly the third organ, skin, is stripped of epidermis and underlying adipose material and the dermis is sectioned into 100–200 µm thick sheets parallel to the dermal surface with a dermatome. It is then freeze-dried, particularized and washed in preparation for combination with cells or transplantation. Alternatively the sheets derived from the jejunum and the dermis can be made porous or perforated with a meshing machine or similar device so that they can be seeded with cells or pseudo-islets or both.

Aggregates can also be formed when suspensions of cultured cells are combined with matrix particulates in a transwell chamber, such as that produced by COSTAR™. The fluid in which the cells and particulates are suspended drains through the porous membrane that serves as the floor of the chamber and the cells are brought into close proximity with the particulates whose surfaces they attach to. Secreted cell products provide the additional matrix that gives the mass of particulates coherence.

Two other approaches to giving the particulate-cell, or particulate-pseudo-islet combinations coherence to facilitate grafting as sheets are the following: A flat porous collagen container, or one made with a poly-l-lactate or other biopolymer, is fabricated and filled with the matrix particulates and adherent cells constituted in a bioreactor or other device. The biopolymer container and its contents can then be maintained in a chamber whose floor is a transwell membrane in contact with nutrient medium.

The other method consists of crosslinking the particulates non-toxically with transglutaminase in the presence of dermatan sulfate and fibronectin thereby forming three dimensional reconstituted tissues. Because this method is not damaging to cells, crosslinking can occur in the presence of cells. The assembled constructs, that is three dimensional reconstituted tissues, are incubated at 37° C. in a 5% $CO_2$ incubator and allowed to undergo differentiation in vitro in preparation for transplantation.

Equivalents

Those skilled in the art will know, or be able to ascertain using no more than routine experimentation, many equivalents to the specific embodiments of the invention described herein. These and all other equivalents are intended to be encompassed by the following claims.

I claim:

1. A thread comprising connective tissue particulates and a polymer, wherein the connective tissue particulates
   a) are derived from a tissue source having living cells;
   b) lack the living cells normally found in the tissue source from which they are derived; and
   c) include factors derived from the tissue source which are necessary for cell growth, morphogenesis, and differentiation.

2. The thread of claim 1, wherein the polymer is bioabsorbable.

3. The thread of claim 2, wherein the polymer is collagen.

4. The thread of claim 3, wherein the collage is porcine fetal collagen.

5. A thread comprising a central core and an outer sleeve, wherein the central core comprises connective tissue particulates which
   a) are derived from a tissue source having living cells;
   b) lack the living cells normally found in the tissue source from which they are derived; and
   c) include factors derived from the tissue source which are necessary for cell growth, morphogenesis, and differentiation;

and the outer sleeve comprises a porous polymer.

6. The thread of claim 5, wherein the polymer is bioabsorbable.

7. The thread of claim 6, wherein the polymer is collagen.

8. The thread of claim 7, wherein the collagen is porcine fetal collagen.

9. A plurality of threads of claim 1 or 5, which are woven, knitted, or braided to form a fabric.

10. The thread of claim 1 or 5 which is seeded with cells.

* * * * *